US006325992B1

(12) United States Patent
Chow et al.

(10) Patent No.: US 6,325,992 B1
(45) Date of Patent: Dec. 4, 2001

(54) CALCIUM PHOSPHATE HYDROXYAPATITE PRECURSOR AND METHODS FOR MAKING AND USING THE SAME

(75) Inventors: Laurence C. Chow, Potomac; Shozo Takagi, Gaithersburg, both of MD (US)

(73) Assignee: American Dental Association Health Foundation, Gaithersburg, MD (US)

( * ) Notice: Subject to any disclaimer, the term of this patent is extended or adjusted under 35 U.S.C. 154(b) by 0 days.

(21) Appl. No.: 09/514,752

(22) Filed: Feb. 28, 2000

Related U.S. Application Data

(60) Continuation of application No. 09/253,644, filed on Feb. 19, 1999, now abandoned, which is a continuation of application No. 08/781,291, filed on Jan. 13, 1997, which is a continuation of application No. 08/471,903, filed on Jun. 7, 1995, now Pat. No. 5,695,729, which is a division of application No. 08/353,075, filed on Dec. 9, 1994, now Pat. No. 5,542,973, which is a division of application No. 08/030,709, filed on Mar. 12, 1993, now Pat. No. 5,522,893.

(51) Int. Cl.⁷ .............................. A61K 7/16; C09K 3/00
(52) U.S. Cl. ......................... 424/49; 423/305; 423/308; 423/311
(58) Field of Search ........................ 524/417, 436, 524/437; 424/49, 696; 623/16; 423/305, 308; 106/35

(56) References Cited

U.S. PATENT DOCUMENTS

| 4,612,053 |   | 9/1986  | Brown et al. .                |
|-----------|---|---------|-------------------------------|
| 5,053,212 | * | 10/1991 | Constantz et al. ...... 423/305 |
| 5,092,888 |   | 3/1992  | Iwamoto et al. .              |
| 5,342,441 | * | 8/1994  | Mandai et al. ............ 106/35 |
| 5,409,982 | * | 4/1995  | Imura et al. ............ 524/417 |
| 5,695,729 | * | 12/1997 | Chow et al. ............ 423/305 |

FOREIGN PATENT DOCUMENTS

| 64-29266  | 1/1989  | (JP) . |
| 1-301543  | 12/1989 | (JP) . |
| 3-183605  | 8/1991  | (JP) . |
| 4-59611   | 2/1992  | (JP) . |

OTHER PUBLICATIONS

English Translation, Japanese Examiner's Citation to References, "Notification of Reason of Rejection", Feb. 2, 1999.
Australian Examiner's Citation to References, Sep. 20, 1996.

* cited by examiner

*Primary Examiner*—Zohreh Fay
*Assistant Examiner*—Brian-Yong Kwon
(74) *Attorney, Agent, or Firm*—Banner & Witcoff, Ltd.

(57) ABSTRACT

Calcium phosphate compositions that are particularly useful and unique as orthopedic and dental cements and remineralizers, as well as methods and kits for their use, and the resulting products are disclosed. The compositions comprise tetracalcium phosphate which has been prepared from a mixture with a calcium to phosphorous ratio of less than 2, or prepared and maintained under substantially anhydrous conditions prior to use or, preferably, both. The novel compositions are converted substantially to hydroxyapatite upon setting, are substantially gradually resorbable and replaced by bone when implanted in contact with living bony tissue, and offer distinct advantages in terms of cement strength, setting time and reliability and other properties.

2 Claims, 3 Drawing Sheets

DIAMETRICAL TENSILE STRENGTH (DTS) OF CEMENT

PERIOD OF EXPOSURE TO 100% HUMIDITY MOIST AIR

X-RAY DIFFRACTION SPECTRA OF TTCP EXPOSED TO 100% HUMIDITY AIR FOR DIFFERENT LENGTHS OF TIME

X-RAY DIFFRACTION SPECTRA OF
TTCP GROUND IN 95% ETHANOL FOR
20 HOURS SHOWING CONVERSION TO OHAp

CALCIUM PHOSPHATE HYDROXYAPATITE PRECURSOR AND METHODS FOR MAKING AND USING THE SAME

CROSS REFERENCE TO RELATED APPLICATIONS

This is a continuation of application Ser. No. 09/253,644 (now abandoned), filed Feb. 19, 1999 which is a continuation of application Ser. No. 08/781,291, filed Jan. 13, 1997 which is a continuation of application Ser. No. 08/471,903, filed Jun. 7, 1995 (U.S. Pat. No. 5,695,729) which is a division of application Ser. No. 08/353,075 filed Dec. 9, 1994 (issued on Aug. 6, 1996 as U.S. Pat. No. 5,542,973) which is a division of application Ser. No. 08/030,709 filed Mar. 12, 1993 (issued on Jun. 4, 1996 as U.S. Pat. No. 5,522,893).

This invention was made in the course of research partially supported by a government grant from the National Institute of Dental Research (Grant No. DE 05030). The U.S. government has certain rights in the invention.

BACKGROUND OF THE INVENTION

1. Field of the Invention

This invention relates to calcium phosphate compositions, including cements, pastes and slurries, and to the methods for making and using them In particular, the invention relates to hydroxyapatite forming cements, pastes and slurries prepared from a set of precursors which includes tetra-calcium phosphate.

2. Description of Related Art

It has been known for some time that hydroxyapatite materials have the basic properties of human bones and teeth. A considerable amount of research has been directed to the remineralization of incipient dental lesions by deposition of hydroxyapatite, $Ca_3(PO_4)OH$, on such lesions, so that the hydroxyapatite is incorporated into the dental structure at the point of lesion.

Remineralization of tooth enamel has been carried out experimentally both in vivo and in vitro. These studies have concentrated on the reminerelizing properties of saliva and synthetic solutions supersaturated with respect to hydroxyapatite. Two articles that give a good overview of this research are Briner et al, "Significance of Enamel Remineralization", J. Dent Re. 53:239–243 (1974); and "Silveritone", "Remineralization Phenomena", Caries Res. 11 (Supp. 1): 59–84 (19771. Additional experimental work in the areas of remineralization of calcium phosphate biomaterials may be found in Gelhard et at. "Rehardening of Artificial Enamel Lesions in Vivo", Caries Res. 13: 80–83 (1979); Hiatt et al., "Root Preparation 1. Obduration of Dentinal Tubules in Treatment of Root Hypersensitivity", J. Periodontal. 43: 373–380 (1972); LeGeros et al, "Apatite Calcium Phosphates: Possible Dental Restorative Materials", IADR Abstract No. 1482 (1982); Pickel et al. "The Effect of a Chewing Gum Containing Dicalcium Phosphate on Salivary Calcium and Phosphate", Ala. J. Med. Sci. 2: 286–287 (1965); Zimmerman et al., "The Effect of Remineralization Fluids on Carious Lesions in Vitro", IADR Abstract No. 282 (1979); and U.S. Pat. No. 3,679,360 (Rubin) and U.S. Pat. No. 4,097,935 (Jarcho).

Generally, the supersaturated solutions or slurries used for remineralization experiments have been prepared from a single form of calcium phosphate. However, these solutions or slurries have been unsatisfactory for a variety of reasons In the area of dental cements, the prior art shows an array of compounds. Some cements, however, irritate the pulp and are unsuitable for applications where the cement must come in contact with exposed pulp. Guide to Dental Materials and Devices, 7th Ed. (ADA 1974) p. 49. One solution to this problem is a cement made of materials similar in composition to tooth and bone mineral, since this would not irritate the living tissue.

The use of $\beta\text{-}Ca_3(PO_4)_3$ was suggested for pulp capping in Driskell et al., "Development of Ceramic and Ceramic Composite Devices for Maxillofacial Application", J. Biomed. Mat. Res. 6: 345–361 (1972); and the use of $Ca_4(PO_4)_2O$ was suggested by Brown and Chow in IADR Abstract No. 120, J. Dent. Res. 54: 74 (1975), as a possible pulp capping agent As described in the latter, $Ca_4(PO_4)_2O$ hydrolyzes to hydroxyapatite.

Such single calcium phosphate cements are incapable of setting to a hard consistency, however, and suffer from the same drawbacks as single calcium phosphate remineralizer. They cannot maintain a relatively constant pH and do not have sufficient remineralization capacity. Though U.S. Pat. No. 3,913,229 (Driskell et al.) discloses putty-like pastes containing $\alpha\text{-}Ca_3(PO_4)_2$, $\beta\text{-}Ca_3(PO_4)_2$, $CaHPO_4$ and mixtures thereof as pulp capping, root canal, and tooth replanting materials, it is believed that none of then pastes harden into cements. Furthermore, no remineralization properties are disclosed and it is believed that none of these pastes are capable of any substantial remineralization.

Experience with calcium-based implants for the replacement of skeletal tissue has also existed for many years. Most of these implants have been in the form of prefabricated, sintered hydroxyapatite in either granule or block forms. These preparations have several drawbacks, including a limited ability to conform to skeletal defects, particularly in the case of blocks; inadequate structural integrity of granules (which do not bond together), and difficulty in modeling the implant to the shape of missing skeletal tissue with both blocks and granules. The block form of hydroxyapatite provides structural support, but among other complications, must be held in place by mechanical means, which greatly limits its use and its cosmetic results; and it is very difficult to saw a shape such that it fits the patient's individual defect. The granular form produces cosmetically better results, but has a very limited structural stability and is difficult to contain during and after a surgical procedure. In general, all of these products are ceramics, produced by high temperature sintering, and are not individually crystalline, but rather have their crystal boundaries fused together. These ceramic-type materials are in general functionally biologically non-absorbable (having an absorption rate generally not exceeding on the order of 1% per year).

A porous, non-resorbable material based on coral allows intergrowth with bone, but ultimately becomes only approximately 20% bone with the remaining 80% subsisting as scar tissue. HA RESORB made by Osteogen is a form of absorbable hydroxyapatite, but is not a cement. It is granular and not adhesive. HA RESORB is loosely rather than adhesively packed into place. For large uses, it is replaced by bone too quickly. In the dental materials market, HAPSET is a composition of calcium phosphate granule and cementable plaster of Paris (calcium sulfate). This material is not truly a hydroxyapatite and contains too much calcium sulfate for most biological uses. The calcium sulfate component of such a composition is resorbable, but not the calcium phosphate granules.

In sum, the commercially available hydroxyapatite materials are in general not resorbable with accompanying replacement by bone, and are not self-setting (self-hardening) cements.

The patent literature, does, however, describe at least one class of calcium phosphate compositions which are precursors for the formation of hydroxyapatite, and which as slurries, offer good remineralization potential; and, as cements, are biologically compatible, self-setting (self-hardening) and substantially resorbable (biodegradable), with bone replacement, when implanted in contact with living bone tissue. See U.S. Pat. Nos. Re. 33,221 and Re. 33,161 to Brown and Chow, which teach preparation of calcium phosphate remineralization compositions and of a finely crystalline, non-ceramic, gradually resorbable hydroxyapatite cement based on the same calcium phosphate composition. Somewhat similar, and in certain instances potentially identical products are described in U.S. Pat. Nos. 5,053,212, 4,880,610, 5,129,905, 5,047,031, and 5,034,059 to Constantz and others, although the use of non-traditional chemical terminology in the latter patents makes interpretation of them and comparison of them with the prior work of Brown and Chow difficult.

The major components of the calcium phosphate remineralizing slurries, pastes and cements taught in U.S. Pat. Nos. Re. 33,221 and Re. 33,161 are preferably tetracalcium phosphate ($Ca_4(PO_4)_2O$), and at least one other sparingly soluble calcium phosphate, preferably dicalcium phosphate anhydrous ($CaHPO_4$), or dicalcium phosphate dihydrate ($CaHPO_4 \cdot 2H_2O$). These react in in aqueous environment to form hydroxyapatite, the principal mineral in teeth and bones, as the final product. Because of the apatitic nature of the set cement, it is highly compatible with soft and hard tissue. This material, if applied intraoperatively as a paste, subsequently sets to a structurally stable implant composed of microporous hydroxyapatite.

SUMMARY OF THE INVENTION

The materials of Brown and Chow U.S. Pat. Nos. Re. 33,221 and Re. 33,161, while highly useful, were characterized by some variation in reproducibility of hardening and generally only moderate mechanical strength for the set hydroxyapatitc. Applicants have discovered that unique steps in the preparation of the tetracalcium phosphate reactant employed in the calcium phosphate composition result in important improvements in the resulting hydroxyapatite. In particular, applicants have discovered that the use of a tetracalcium phosphate precursor which has a calcium to phosphate ratio less than 2 results in a cement which sets more reliably and more quickly to provide a superior product. Applicants have also discovered that calcium phosphate cements with substantially improved setting times and mechanical strengths are obtained when tetracalcium phosphate is prepared under anhydrous conditions. The resulting cements set reliably with concomitant strength attainment. The setting rate can be adjusted for various end uses and may be quite rapid if desired. The inventive hydroxyapatite cement is both biocompatible and resorbable (biodegradable) with bone replacement when in contact with living bone.

The invention includes a calcium phosphate composition, which self-hardens substantially to hydroxyapatite at ambient temperature when in contact with an aqueous medium, comprising tetracalcium phosphate and at least one other sparingly soluble calcium phosphate compound, wherein the tetracalcium phosphate is prepared from a starting mixture of one or more sources of calcium, phosphorous and oxygen which mixture has a calcium to phosphorous ratio of less than 2. The invention further includes a calcium phosphate composition, which self-hardens substantially to hydroxyapatite at ambient temperature when in contact with an aqueous medium, comprising tetracalcium phosphate and at least one other sparingly soluble calcium phosphate compound, wherein the tetracalcium phosphate is prepared and maintained under substantially anhydrous conditions prior to its contact with the aqueous medium in combination with the sparingly soluble calcium phosphate compound. Alternatively, the inventive calcium phosphate cement's tetracalcium phosphate component may have both these characteristics. The invention includes formulations for increasing the remineralization potential of saliva, and dental restoratives employing the new tetracalcium phosphate-containing compositions.

The invention also includes an improved method for preparing a self-hardening calcium phosphate cement comprising combining tetracalcium phosphate and at least one other sparingly soluble calcium phosphate, in which the synthesis mixture for preparation of the tetracalcium phosphate component has a calcium to phosphate ratio of less than 2. Alternatively, or in combination, the invention includes a significantly improved method for preparing a self-hardening calcium phosphate cement comprising combining tetracalcium phosphate and at least one other sparingly soluble calcium phosphate in which the tetracalcium phosphate precursor is prepared and stored under anhydrous conditions. The invention further contemplates the improved calcium phosphate cements prepared by this method, the cement component(s) provided to the user in a pre-manufactured kit or delivery device, the methods of using the improved cement, and the biological implants made from the cement. A self-hardening industrial cement is also contemplated.

The techniques previously available for repair of cranio- and maxillofacial defect, periodontal defects, bone fractures and other dental and orthopedic defects which could not be successfully self-healed relied heavily on the use of metallic and ceramic inserts and prostheses which might remain indefinitely as foreign object in the body of a human or veterinary patient. As such, these prior art techniques suffered from a host of related problems, including possible rejection, sites for infection, structural failure, injury to neighboring tissue and the like. Metals are difficult to shape and are hampered by problems such as infection and corrosion Polymers such as silicone, PROPLAST, or methylmethacrylate are encapsulated by scar tissue resulting in significant rates of implant infection and/or extrusion Biologic materials, such as autogenous bone grafts, may cause donor site morbidity, may suffer from significant post-implantation resorption, and are difficult to accurately conform to skeletal defects. U.S. Pat. Nos. Re. 33,221 and Re. 33,161 offer the alternative of a hydroxyapatite-forming calcium phosphate cement which is biocompatible and which when implanted in contact with living bone, is largely if not completely replaced by now bone formation, with no significant loss in the volume or integrity of the tissue that receives the implant. The above-cited patents to Brown and Chow teach the preparation of such bioresorbable cements preferably from combinations of tetracalcium phosphate ($Ca_4(PO_4)_2O$) and another sparingly soluble calcium phosphate compound, preferably dicalcium phosphate or dicalcium phosphate dihydrate.

The inventive slurries, pastes and cements described and claimed herein are characterized by many important advantages as compared with traditional hydroxyapatite materials. While the inventive materials are of the same general class as those of Brown and Chow, cited above, and maintains the latter's advantages they also contributes additional unexpected advantages.

The tetracalcium phosphate prepared and maintained under anhydrous conditions is not contaminated at the crystal surfaces by the less soluble reaction products of tetracalcium phosphate and moisture. The tetracalcium phosphate prepared and maintained under anhydrous conditions is thus believed to be more readily soluble than ordinary tetrtcalcium phosphate, promoting the quicker release of calcium and phosphate moieties in slurry applications.

With respect to Cement applications, the hydroxyapatite cement described and claimed herein sets more quickly, reliably and reproducibly. If other factors (e.g., composition of the liquid phase, powder to liquid ratio, temperature and powder particle size) are held constant at typical values the inventive cement is reliably fast-setting; in the presence of water or a dilute aqueous acid or base solution, it will set reproducibly in about 15–30 minutes, typically about 25 minutes, and will fully convert (precipitate) to a solid mass of hydroxyapatite in situ within 4–6 hours.

The novel cement is also characterized by significantly improved mechanical strength properties. While the inventive hydroxyapatite cement, without augmentation, may not have sufficient shear-strength resistance to function in the reconstruction of stress-bearing bones, the cement is sufficiently structurally stable for reconstruction and augmentation of relatively non-stress-bearing bony tissue.

Additional advantageous attributes of the inventive cement include the following:

The cement is easy to use. It can be mixed with water, blood, saline, dilute phosphoric acid, or other agents to provide malleability and create a paste or putty. The liquid employed may be only that liquid present at the site where the cement is to be applied, such as blood or saliva. The cement can then be easily modeled to accurately reconstruct bony cavities and missing bone and to recreate contour defects of relatively non-stress bearing skeletal bone.

The cement or paste consistency enables the hydroxyapatite to conform exactly to the contours of the defect. The cement can be applied to the defect, e.g., with a spatula, can be molded and sculpted, and will hold its shape satisfactorily until set.

The inventive cement sets at ambient temperature, e.g., room or body temperature, unlike the ceramic-type calcium phosphate cements which must be sintered at high temperature in a process that fuse individual hydroxyapatite crystals to each other. The cement setting reaction for the inventive material is isothermic (negligible beat is generated) and thus does not result in heat-generated necrosis of any of the neighboring tissue The inventive cement can be easily sculpted in vivo (intrioperatively) even after setting. When applied to clean, non-infected bone, the cement adheres to the bone, thereby greatly increasing its possible applications. In general, the cement can be adapted to many applications.

The inventive cement represents a highly biocompatible tissue substitute precursor or synthetic implant material for skeletal reconstruction. This biocompatibility stems from the fact that calcium phosphate exists in bone in the form of hydroxyapatite, and it is therefore a chemically natural material. Basically, the inventive cement is regarded by the body as a native material; it triggers no significant or sustained inflammatory response, and no foreign body giant cell reaction.

The absence of fibrous encapsulation and minimal inflammation compare favorably with what is seen with polymer implants such as methylmethacrylate or PROPLAST, and aid in minimizing the potential for infection and implant loss. The inventive cement is non-toxic and non-carcinogenic (non-mutagenic).

Finally, the inventive cement can undergo gradual biointegratiom. When in contact with viable bone or periosteum, although there is no significant change in implant shape or volume over time, the cement is gradually replaced over the course of weeks and months, at least in part, with osseous tissue, on an approximately 1:1 basis as the implant is resorbed. The cement actually promotes the growth of living bone into the implant, and this osteointegration of the cement with the surrounding bone with variable replacement of the implant by living bone over time results in permanent fusion and further structural stability. The cement is thus remodelled gradually in a manner that resembles the remodeling of living bone. The finely crystalline microporous structure of the implants, which facilitates osteoblast penetration, also permits ion passage, but prevents bacteria from permeating the implant.

DESCRIPTION OF THE PREFERRED EMBODIMENTS

Figure 1:
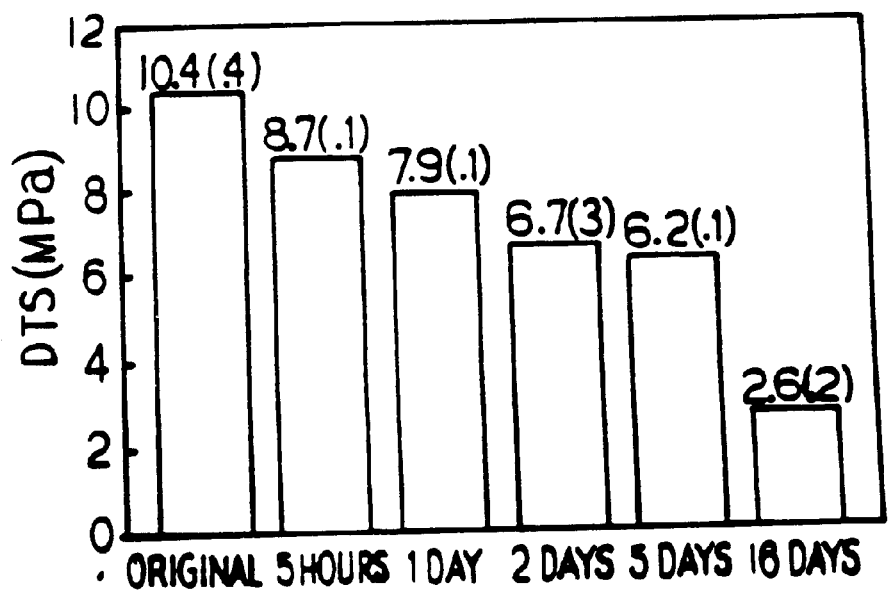
FIG. 1 is a graph of the mean diametral tensile strength of calcium phosphate cement specimens prepared using, as the tetracalcium phosphate component, tetracalcium phosphate that had been exposed to 100% humidity air for different periods of time.

The complete disclosures of U.S. Pat. Nos. Re. 33,221 and Re. 33,161 are expressly incorporated herein by reference.

The inventive hydroxyapatite cement is an improvement on the selfsetting cement of calcium phosphate compounds developed by Brown and Chow. The preferred major components of the calcium phosphate cement of Brown and Chow are tetracalcium phosphate (TTCP) and dicalcium phosphate anhydrous (DCPA) or dicalcium phosphate dihydrate (DCPD). These react in an aqueous environment to form hydroxyapatite (OHAp), the principal mineral component of teeth and bones, as the final product

$$Ca_4(PO_4)_2 + CaHPO_4 \text{ (or } CaHPO_4 \cdot 2H_2O) \rightarrow Ca_5(PO_4)_3OH$$

The results from extensive in vitro and in vivo studies suggest that the usefulness of calcium phosphate cement can be further advanced if the following two areas of the cement properties are improved: (1) shorter and more consistent setting times and (2) greater mechanical strengths.

Described in the following are novel procedures for preparing tetracalcium phosphate and resulting selfsetting calcium phosphate cements with greatly improved properties Aspects of the invention include (1) the calcium (Ca) to phosphate ($PO_4^s$ or P) molar ratio in the prepared tetracalcium phosphate should be below 2, and/or (2) the tetracalcium phosphate is kept under a substantially anhydrous environment during its synthesis, quenching, particle size reduction process and storage.

If the prepared tetracalcium phosphate has a molar Ca/P ratio above 2, calcium oxide is believed to be present in the material as an impurity phase. When such a tetracalcium phosphate sample is used in the cement, the rapid dissolution of the CaO causes the pH of the cement slurry to rise substantially above pH 8.5 (but below 12), which impedes the setting reaction.

It has also been found that tetracalcium phosphate is extremely reactive to water. Thus, when exposed to air, tetracalcium phosphate has been found to react with the moisture present in the air to form a small amount of hydroxyapatite (OHAp) and calcium hydroxide or calcium oxide. It has been discovered that these products coat the surfaces of the tetracalcium phosphate crystals and cause the tetracalcium phosphate particles to become significantly less reactive when used in the cement system. By maintaining tetracalcium phosphate in an anhydrous environment, the undesirable surface contamination by the aforementioned reaction products is minimized. Self-setting calcium phosphate cements with substantially improved setting times and mechanical strengths were obtained when tetracalcium phosphate prepared under anhydrous conditions was used.

The undesirable reaction of tetracalcium phosphate with moisture is irreversible at later stages in its preparation so that drying the moisture-exposed tetracalcium phosphate to is remove the water would not suffice to reclaim the properties of uncontaminated tetracalcium phosphate.

Tetracalcium phosphate has the formula $Ca_4(PO_4)_2O$, and a theoretical ideal molar Ca/P ratio of 2.0. Its traditional mode of preparation is illustrated in the following equation:

$$2CaHPO_4+2CaCO_3 \rightarrow Ca_4(PO_4)_2O+H_2O\uparrow+2\ CO_2\uparrow \quad (1)$$

It is thermodynamically stable only at temperatures above approximately 1400° C.

The inventive preparation of tetracalcium phosphate powder for cement use is illustrated by the following steps:

EXAMPLE 1
Preparation of Tetracalcium Phosphate in a Furnace:

To prepare an embodiment of the inventive tetracalcium phosphate one first prepares a homogenous mixture that has a Ca/P ratio of less than 2, heats the mixture to 140° C. or above, and then maintains the sample at that temperature for a sufficiently long period of time, for example 6 hours, to assure as complete conversion as possible of the starting mixture to tetracalcium phosphate. An example of the starting mixture would consist of 2 moles of $CaHPO_4$ (272 grams) and 1.8 moles of $CaCO_3$ (180 grams). The excess $H_2O$ and $CO_2$, are expelled in the heating process One may also use any other types of calcium and phosphate containing compounds to prepare mixtures with a molar Ca/P ratio of less than 2 provided that the non-calcium and non-phosphate components in the mixture can be expelled by evaporation during the firing with or without an accompanying oxidation reaction. For example, the following reactions may be employed with appropriate adjustment of the molar ratios:

$$2CaHPO_4+2CaO \rightarrow Ca_4(PO_4)_2O+H_2O\uparrow \quad (2)$$

$$Ca_3P_2O_7+2CaO \rightarrow Ca_4(PO_4)_2O \quad (3)$$

$$Ca_3(PO_4)_3+Ca(OH)_3 \rightarrow {}^3Ca_4(PO_4)_2O+H_2O\uparrow \quad (4)$$

$$4CaO+2(NH_4)_3PO_4 \rightarrow Ca_4(PO_4)_3O+6NH_3\uparrow+3H_2O\uparrow \quad (5)$$

$$2CaHPO_4+2Ca(CH_3CO_2)_2+4O_2 \rightarrow Ca_4(PO_4)_2O+7H_2O\uparrow+4CO_2\uparrow \quad (6)$$

The preparation of the mixture for firing is the only step in the tetracalcium phosphate synthesis in which the presence of water is not a concern. This is because the tetracalcium phosphate is formed only after the firing process.

EXAMPLE 2 (COMPARATIVE)

If the Ca/P molar ratio of the homogenous mixture prepared for firing is above 2, calcium oxide will be present as an impurity phase in the product. Thus, in the reaction represented by equation (1), if 2 moles (272 grams) of $CaHPO_4$ is combined with 2.2 moles (220 grams) of $CaCO_3$, the molar Ca/P ratio will be 2.1, and the reaction in the furnace will be:

$$2CaHPO_4+2.2CaCO_3 \rightarrow Ca_4(PO_4)_2O+0.2CaO+H_2O\uparrow+2.2CO_2\uparrow \quad (7)$$

The presence CaO as an impurity in the prepared tetracalcium phosphate is undesirable because during the cement setting, rapid dissolution of CaO raises the slurry pH to approximately 10 to 12, and this greatly impedes the setting reaction to the point that the cement often fails to harden.

EXAMPLE 3

While it is essential that Ca/P ratios of greater 2 should be avoided, a mixture with a ratio of lower than 2 is permissible, as far as the cement setting reaction is concerned. This is because in such a case, the reaction impurity by-product will be hydroxyapatite. It is important to note that when hydroxyapatite is formed during the firing process it is homogeneously dispersed in the prepared tetracalcium phosphate as a phase impurity, and the reactivity of tetracalcium phosphate is not significantly affected. This is in great contrast to the hydroxyapatite coatings that form on the tetracalcium phosphate crystals as a result of reaction with moisture. In this latter case, the hydroxyapatite is highly detrimental to the reactivity of tetracalcium phosphate. Equation (8) given below illustrates the hydroxyapatite as a by-product when a mixture with a Ca/P ratio of 1.9 is fired:

$$2CaHPO_4+1.8CaCO_3 \rightarrow 0.7Ca_4(PO_4)_2O+0.2Ca_8(PO_4)_3OH+H_2O\uparrow+1.8CO_2\uparrow \quad (8)$$

EXAMPLE 4

A Ca/P ratio of 2 precisely is to be avoided because the inherent error in measurement of the reactants takes actual preparation of a sample with Ca/P ratio greater than 2 a statistical probability in a number of instances, and because cements prepared from tetracalcium phosphate with Ca/P ratio less than 2 have been found to have greater mechanical strength than those with a ratio of 2, as illustrated in the following table:

TABLE I

Effect of the Ca/P Ratio of TTCP on Diametral Tensile Strength (DTS) of Calcium Phosphate Cement

| Ca/P Ratio of TTCP | 2.0 | 1.96 | 1.90 |
|---|---|---|---|
| DTS (MPa) Mean ± s.d. (n = 3) | 8.34 ± 0.17 | 8.06 ± 1.64 | 10.38 ± 0.44 |

To prepare the calcium phosphate cement, tetracalcium phosphate and dicalcium phosphate anhydrous were combined at a molar ratio of 1:1, and mixed with 25 mmol/L phosphoric acid at a powder to liquid weight ratio of 4.0 at ambient temperature.

Diametral tensile strength was measured as follows:

DTS measurement: 0.3 gram of calcium phosphate cement powder was mixed with 0.075 mL of liquid (powder/ liquid=4), spatulated on a glass slab for 30 sec. and placed in a stainless steel mold (6 mm d×3 mm h). The top and bottom surfaces of the mold were tightly covered with glass plates and the mold was placed in a 100% humidity box kept at 37° for 4 hours. The sample was removed from the mold and placed in a small amount of water for 20 hours at 37°. The diametral tensile strength (DTS) was measured with the use of a Universal. Testing Machine (United Calibration Corp, Garden Grove, Calif.) at a cross-head speed of 1 mm/min.

As a practical matter, the Ca/P ratio must remain above 1.679 or stoichiometry dictates the preparation of hydroxyapatite rather than tetracalcium phosphate. Therefore, in this context, "less than 2" should be interpreted herein to mean lea than 2 but greater than 1.67.

EXAMPLE 5

Quenching of Fired Mixture in an Anhydrous Atmosphere:

After heating the mixture for a sufficient length of time, the mixture must be cooled down rapidly to prevent reversion of the tetracalcium phosphate to the phases that are more stable than tetracalcium phosphate at temperatures lower than 1400° C. If the tetracalcium phosphate were cooled down slowly, for example, by letting it cool down spontaneously in a furnace that has been turned off, the product obtained would contain little tetracalcium phosphate. Instead, it would be a mixture that would additionally contain hydroxyapatite, calcium oxide, α-tricalcium phosphate, β-tricalcium phosphate, or calcium pyrophosphate, depending on the Ca/P ratio and the rate of cooling. Such a sample, if used for preparing the cement, would yield a product with poor setting and strength properties. Therefore, quenching is necessary, and it must be done under a substantially anhydrous environment. One example of a suitable anhydrous quench technique would be to place the mixture, as soon as it is no longer red hot, in a vacuum desiccator to isolate the tetracalcium phosphate from moisture. Other techniques of anhydrous quenching available to those of skill in the art may be used.

If the tetracalcium phosphate is quenched in an atmosphere that contains moisture, a reaction illustrated by equation (9) or (10) will occur and the tetracalcium phosphate crystals will become coated with the reaction products, hydroxyapatite and $Ca(OH)_2$ or CaO. Such a tetracalcium phosphate sample will have poor reactivity when used in the cement formulation.

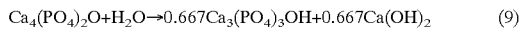

$$Ca_4(PO_4)_2O + H_2O \rightarrow 0.667Ca_3(PO_4)_3OH + 0.667Ca(OH)_2 \quad (9)$$

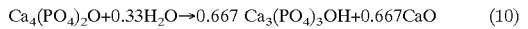

$$Ca_4(PO_4)_2O + 0.33H_2O \rightarrow 0.667\,Ca_3(PO_4)_3OH + 0.667CaO \quad (10)$$

Exposure to moisture at this stage will cause damage to the tetracalcium phosphate's reactivity to a significant extent, although not as critical as in the later stages of the preparation. This is because at this point, the tetracalcium phosphate is the form of chunks or lumps, with relatively small surface areas amenable to contamination, as compared with the tetracalcium phosphate that has been processed to a fine-particle state. However, moisture absorbed in the uncomminuted tetracalcium phosphate may produce an adverse effect in the comminution process as described below.

EXAMPLE 6

Particle Size Reduction.

To produce calcium phosphate cement with the desirable properties, sparingly soluble calcium phosphates of a variety and/or mixture of particle sizes may be used. For many applications, it is preferred that the tetracalcium phosphate have at least a substantial percentage of particles, e.g., at least about 10%, of median particle size of 15 μm or below. In some applications, such as formulating an injectable root canal filler, tetracalcium phosphate with a median particle size of 1 μm or below would be preferred. Therefore, the particle size of the tetracalcium phosphate prepared in Example 5 above needs to be reduced by mechanical means. A substantially anhydrous environment during the particle size reduction process is critical. Small samples of the tetracalcium phosphate may, for example, be comminuted by hand grinding in room air for a brief period, e.g., 5 min, but long exposure to room air would be unacceptable. If the tetracalcium phosphate is ground in a ball mill, it must be done in a closed container to isolate the tetracalcium phosphate from the large volume of moist room air, or in a non-aqueous liquid that has been made anhydrous. Some of the liquids that can be advantageously employed arc cyclohexane, dioxane, and absolute ethanol Other non-aqueous liquids may also be used. Traces of water in these liquids should be removed by molecular sieve or other suitable desccicants. Liquids that should not be used include water, 95% ethanol, other alcohol solutions that contain water, acetone (which generally contains some water), etc. If one of the latter liquids is used the ground tetracalcium phosphate will contain poorly crystallized hydroxyapatite and calcium hydroxide or calcium oxide. Such a sample will produce a poor quality cement or a cement mixture that will not harden. Once the ground tetracalcium phosphate is exposed to moisture and the reaction products coat the tetracalcium phosphate crystal surfaces the reactivity of the tetracalcium phosphate sample cannot be rejuvenated at this point by heating and removing the adsorbed moisture.

As mentioned earlier, if the uncomminuted tetracalcium phosphate contains absorbed moisture, because of the limited surface area, the damage to the tetracalcium phosphate's reactivity as a result of hydroxyapatite coating formation would be significant but perhaps not critical. However, when such a tetracalcium phosphate sample is comminuted in an anhydrous liquid, the moisture released from the contaminated tetracalcium phosphate into the liquid will facilitate the undesirable reaction depicted by equation (9) or (10). This usually will render the tetracalcium phosphate unusable for cement formulation. If it is suspected that the uncomminuted tetracalcium phosphate has been exposed to moisture, and it is to be ground in an anhydrous liquid, it should be heated at 200° C. for 24 hours to remove absorbed moisture and cooled to room temperature in an anhydrous environment before grinding.

EXAMPLE 7

Storage of Ground Tetracalcium Phosphate.

It is important that the ground tetracalcium phosphate be stored in an anhydrous environment. Because the ground tetracalcium phosphate would have relatively large surface area, surface contamination by the reaction products with moisture will substantially compromise the reactivity of the tetracalcium phosphate and the quality of the cement. Once the surface contamination products are formed in substantial quantities, the reactivity of the tetracalcium phosphate cannot be rejuvenated by heating.

The detrimental effects of moist TTCP on the diametral tensile strength of the set cement are illustrated by Table II.

TABLE II

Diametral Tensile Strength of Calcium Phosphate Cement Prepared with Tetracalcium Phosphate that Had Been Exposed to 100% Humidity for Different Lengths of Time

| Length of Exposure in Days | Diametral Tensile Strength mean ± s.d. (n = 3) in MPa |
| --- | --- |
| 0 | 10.38 ± 0.44 |
| 0.2 | 8.71 ± 0.10 |
| 1 | 7.85 ± 0.13 |
| 2 | 6.66 ± 0.25 |
| 5 | 6.26 ± 0.07 |
| 16 | 2.63 ± 0.24 |

Calcium phosphate cement powders were prepared by thorough mixing of 3.66 grams of tetracalcium phosphate and 1.36 grams of dicalcium phosphate. The tetracalcium phosphate had a median particle size of 10.2 $\mu$m and had been exposed to humid air for various periods as indicated. The dicalcium phosphate had a median particle size of 0.1 $\mu$m The diametral tensile strengths were measured following the same procedure as described earlier.

Figure 2:
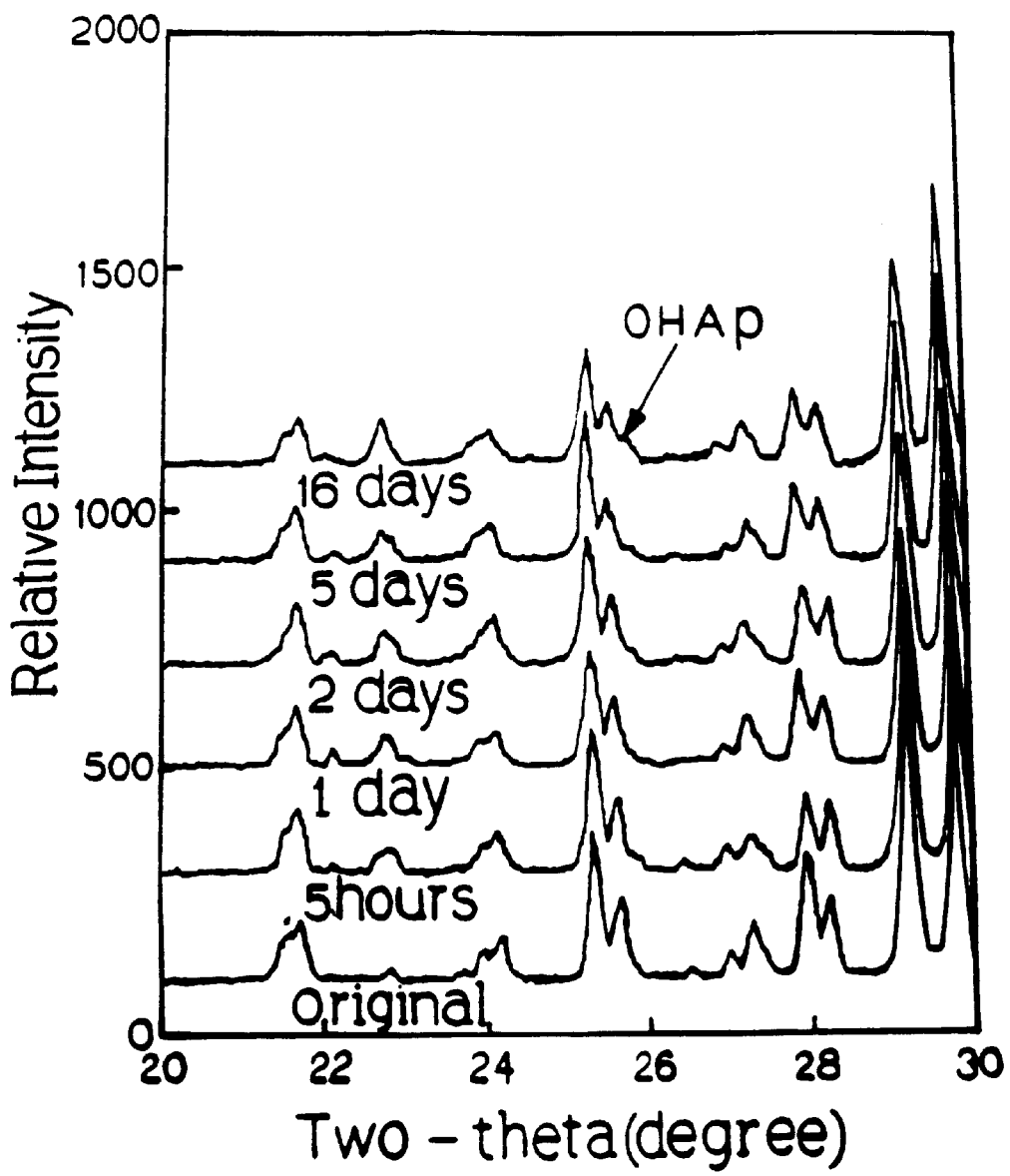
FIG. 2 shows the x-ray diffraction spectra of tetracalcium phosphate exposed to 100% humidity for different periods of time, illustrating the growth in the hydroxyapatite spectral shoulder with increasing moisture exposure.
Figure 3:
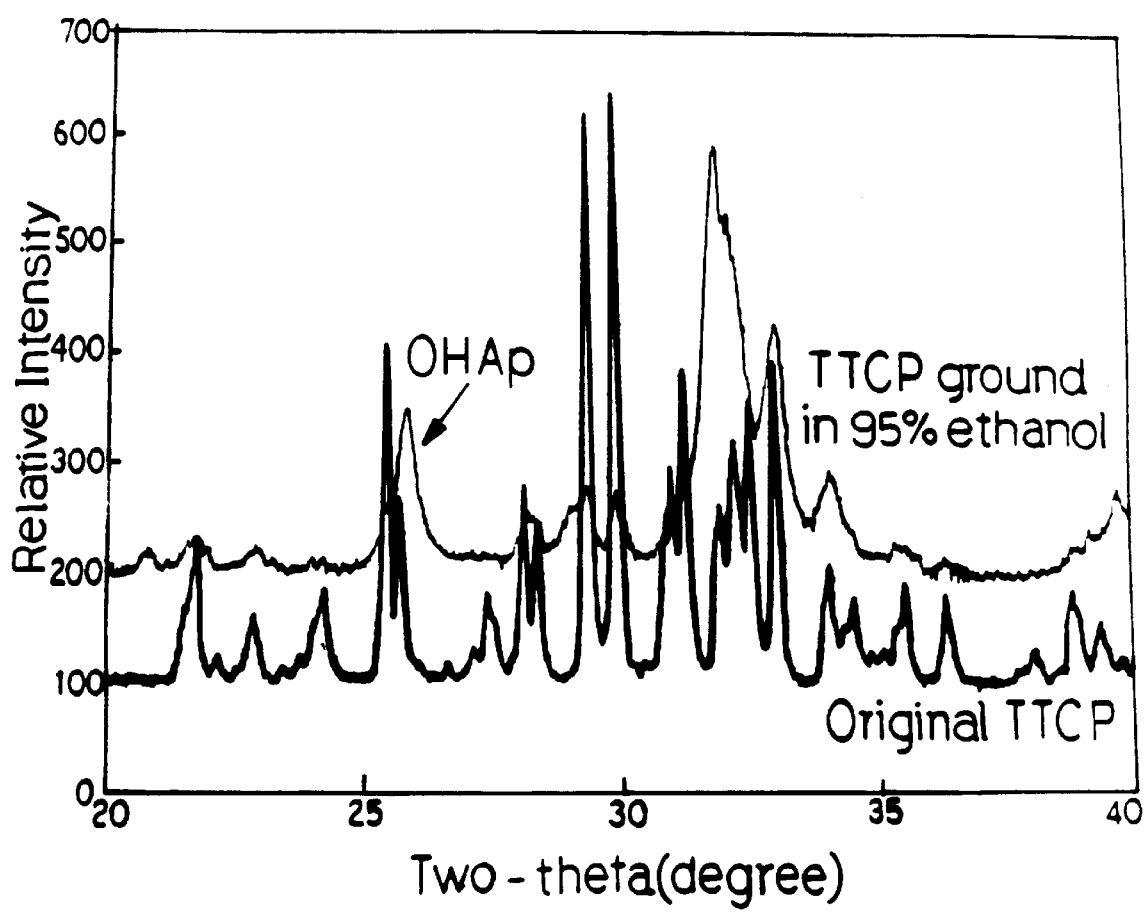
FIG. 3 is the x-ray diffraction spectrum of tetracalcium phosphate prior to grinding and after grinding in 95% ethanol for 20 hours. It illustrates the (undesirable) premature formation of hydroxyapatite.

FIGS. 1–3 also illustrate the formation of hydroxyapatite in TTCP exposed to moist air and its effects. FIG. 1 depicts by bar graph the diametral tensile strength of samples prepared as described above with a TTCP Ca/P ratio of 1.90, but with the indicated periods of exposure of TTCP to 100% humidity air at 37° C.

FIG. 2 gives the x-ray diffraction spectra of TTCP prepared from a mixture with Ca/P=1.90, and then exposed to 37° C. 100% humidity air for the indicated lengths of time. For the x-ray diffraction studies depicted in the figures, cement samples were first made into a fine powder form by hand grinding with the use of a mortar and pestle. Approximately 0.25 grams of ample was placed on the sample holder. A computer-controlled powder x-ray diffractometer (Rigaku, Danvers, Mass.) with CuKs radiation generated under the conditions of 40 kv and 25 mA was used to obtain the XRD patterns. Data were collected in the 2 $\theta$ scanning mode using a step width of 0.01° and count time of 2 sec. Growth of the hydroxyapitite impurity shoulder with increasing moisture exposure of the TTCP is illustrated.

FIG. 3 illustrates by x-ray diffraction spectra the formation of hydroxyapatite impurity in TTCP ground in 95% ethanol for 20 hours. 20 g of TTCP was ground in 50 mL of 95% ethanol in a 250 mL-size agate jar that also contained 50 1-cm diameter agate balls. The grinding was done with the use of a planetary ball mill (Retsch model PM4, Brinkman Instruments, Westbury, N.Y.) for a total of 20 hours. The ground TTCP was dried in a 70° C. vacuum oven for 2 days.

Additional properties of improved calcium phosphate cement as compared with the original calcium phosphate cement of Brown and Chow are listed in Table III:

TABLE III[1]

| | Improved CPC (TTCP Ca/P = 1.90; anhydrous prep) | Original CPC (TTCP Ca/P = 2.0) |
| --- | --- | --- |
| Compressive strength | 64.8 ± .8 MPa (n = 3) | 36.0 ± .7 (n = 5) (Fukase, 1990)[2] |
| Diametral strength | 13.1 ± 1.3 MPa (n = 8) | 6.9 ± .3 (n = 5) |
| Setting time: | 14 min. | 25 |
| Gilmore needle method | | (Brown and Chow, 1986)[3] |

[1]Moles TTCP: Moles DCPA = 1:1, powder/liquid (by wt.) = 4.0, liquid phase = 25 mmol/L $H_3PO_4$ testing conditions as per Example 4.
[2]Fukase et al., "Setting Reactions and Compressive Strengths of Calcium Phosphate Cements," J. Dent. Res. 69 (12): 1852–56 (1990).
[3]Brown, W. E. and Chow, L. C. (1988): A New Calcium Phosphate, Water Setting Cement, Cements Research Progress 1986, P. W. Brown, Ed., Waterville, Ohio: American Ceramic Society, pp. 352–379.

As will be recognized by those of skill in the art, other specific techniques for preparation of the tetracalcium phosphate component of the inventive cement may be employed so that the calcium to phosphate ratio of the tetracalcium phosphate is less than two, and/or the preparation (particularly once the tetracalcium phosphate has been comminuted) is substantially anhydrous. While either the recommended reduction in calcium to phosphate ratio or anhydrous preparation will improve the setting time and quality of the hydroxyapatite cement, the best results are obtained when both methods are practiced together. The inventive methods can be safely practiced in a laboratory or manufacturing facility without imposing excessive additional expenses. The new methods of preparation of tetracalcium phosphate produce cements with shorter and more consistent setting times and substantially greater mechanical strengths.

The inventive calcium phosphate cement is preferably prepared from the tetracalcium phosphate described above and one or more additional sparingly soluble calcium phosphates, particularly dicalcium phosphate anhydrous, dicalcium phosphate dihydrate, $\alpha$-tricalcium phosphate, $\beta$-tricalcium phosphate, amorphous calcium phosphate, and octacalcium phosphate. Most preferably, tetracalcium phosphate is employed with dicalcium phosphate anhydrous or dicalcium phosphate dihydrate. The invention is practiced when the tetracalcium phosphate employed with the second sparingly soluble calcium phosphate compound is prepared in accordance with these conditions whether or not it is generated in situ from other precursors or passes through chemical intermediated. These compounds are contemplated as part of the inventive composition regardless of the nomenclature used to identify them, e.g., "calcium deficient calcium phosphate compounds" instead of dicalcium phosphate.

The specially prepared tetracalcium phosphate and other sparingly soluble calcium phosphate compound(s) are combined with a liquid phase to form the useful cement, paste or slurry. The liquid phase is aqueous at least in part and may typically be water, saline, blood, dilute phosphoric acid, or one of the above with the addition of up to 10% of a calcium or phosphate source in the calcium phosphate cement powder or in the liquid phase itself. In situ liquid, e.g., at a wound site, can suffice.

EXAMPLE 8

Additional calcium phosphate cement compositions that consisted of TTCP prepared in accordance with the invention and one other calcium phosphate from the group consisting of $\alpha$-tricalcium phosphate ($\alpha$-TCP), $\alpha$-tricalcium phosphate ($\beta$-TCP), amorphous calcium phosphate (ACP), and octacalcium phosphate (OCP) were prepared with a liquid phase of 1.5 mol/L $Na_2HPO_4$. This phosphate level in the liquid phase can be attained by adding up to 10% of a phosphate salt in the calcium phosphate cement powder as described in U.S. Pat. Nos. Re. 33,161 and 33,221. Properties of calcium phosphate cements that consisted of TTCP and a calcium phosphate other than DCPA or DCPD are given in Table IV below.

TABLE IV

| Solid component | P/L[1] | DTS[2], MPa (mean ± s.d.; n = 3) | setting time (min) |
|---|---|---|---|
| TTCP[3] + 2 α-TCP | 3 | 1.29 ± .26 | 25 |
| TTCP[3] + 2 β-TCP | 3 | 0.22 ± .17 | 90 |
| TTCP[3] + 2 ACP | 2.5 | 0.88 ± .11 | 15 |
| 3 TTCP[3] + 2 OCP | 3 | 0.48 ± .06 | 90 |

[1]Powder to liquid ratio (by weight)
[2]Diametral tensile strength
[3]Ca/P = 1.90

The above calciums phosphate cement formulation while not preferred because of their relatively low strengths did harden. Some improvements in strengths are likely with adjustment of particle size, powder to liquid ratio and other parameters. These formulations did not set quickly, e.g., 2 hours, when water, saline, or a dilute phosphoric acid was used as the liquid phase in place of the 1.5 mol/L $Na_2HPO_4$.

Generally the preferred cement will be comprised of an equimolar mixture of tetracalcium phosphate and dicalcium phosphate, although TTCP/dicalcium phosphate ratios may range from 1:1 to about 1:4. Calcium phosphate cement that has a TTCP/DCPA ratio of 1.0 will have the stoichiometry of hydroxyapatite. Experimental data now show that cement setting can occur when the ratio is as low as 0.33 or lower. Furthermore, the presence of excess DCPA does not lead to residual DCPA in the end product, the product is apatitic, probably a calcium deficient apatite that has poor crystallinity and greater solubility. Such material may have different in vivo characteristics from that of stoichiometric hydroxyapatite produced by calcium phosphate cement with a TTCP/DCPA ratio of 1.0, perhaps resorbing more rapidly in bone.

The inventive cement may be supplied to the user in a variety of forms, including as powders or as a powder mixture which is later mixed with a diluent such as water or blood to make putty; or as a pre-mixed putty which may contain a nonaqueous extender, e.g., glycerin and/or propylene glycol. It may be supplied with or in the instrumentation which is used to introduce the cement into the body, for example, a syringe, percutaneous device, "gun", cannuls, biocompatible packet, denture, reamer, file, or other forms which will be apparent to those of ordinary skill in the art. It is contemplated that the cement, in any of these forms, may be made available to the surgeon, veterinarian or dentist via a kit containing one or more of its key component. The cement is generally provided or employed in a sterilized condition. Sterilization may be accomplished, e.g., by gamma-ray radiation, typically at a dope of 2.5 Mrad The inventive cement may be employed in a variety of medical, dental and veterinarian procedures to substitute for missing or defective bone or tooth tissue. For example, the cements of the present invention may be used in place of any of the cements known in the prior art a: (i) cavity bases and liners to protect the pulp, (ii) materials for capping exposed pulps, (iii) materials to replace or promote regeneration of bone mineral lost due to periodical disease, (iv) direct filling materials (may be temporary) that have physical properties similar to enamel and are adhesive to enamel and dentin, (v) a cement to build up alveolar ridges in edentulous patients, (vi) an endodontic filling material for root canals, (vii) a material to cement retention pins, (viii) a material for filling sockets after a tooth extraction, (ix) a replacement of bone that has been removed surgically or lost due to trauma, (x) a cement for implanting or replanting teeth, (xi) a luting cement in dentistry and orthopedic surgery, (xii) an investment mold material, (xiii) a material which will promote bone mineral in its vicinity, (xiv) a remineralizing polish for use in place of pumice, and (xv) a root cement for remineralizing and desensitizing of exposed root surfaces, (xvi) a cement for orthopedic prostheses, (xvii) a tooth implant, (xviii) a device for percutaneous passage of tubes, wires and other medical instruments through the skin, and (xxix) a replacement material for bone loss due to abscess. Slurries of calcium phosphate cement may be used to repair bone damage caused by osteoporosis. Reconstruction of cleft palate and other congenital skeletal defects is contemplated with use of the inventive cement, as are other forms of reconstructive and cosmetic surgery.

Various additives may be included in the inventive cements, slurries and pastes to adjust their properties and the properties of the hydroxyapatite products made from them. For example, in addition to the calcium and phosphate containing compounds and dilute acids and bases which may be added to adjust the Ca/P ratio and pH; proteins, medicaments, supporting or strengthening filler materials, crystal growth adjuster, vivacity modifier, pore forming agents and other additives may be incorporated without departing from the scope of this invention.

The novel implants thus prepared are also contemplated as part of the present invention. Where such implants contact living bone tissue, it is believed that the lack of fusion of the hydroxyapatite crystallites resulting from the setting reaction of the inventive cement allows osteoclats to slowly resorb the implants over time. The implants are sufficiently resistant to resorption, however, so that the osteoclasts appear to regard the implants as disorganized bone rather than a synthetic material. Because of this, the implant is slowly resorbed as compared with other calciumbased cements, thus leaving woven bone deposits in its stead.

Since the inventive cements are fully compatible with living tissue, they are especially advantageous where contact with living tissue is necessary. Clinical use of the inventive cement is illustrated in the following example:

EXAMPLE 9

A seventy-year-old female patient suffered from chronic sinus disease so advanced it had dissolved a quartersized portion of the bone of her forehead. The inventive calcium phosphate cement was prepared from an equimolar mixture of tetracalcium phosphate and dicalcium phosphate powders mixed with water. The tetracalcium phosphate employed had a Ca/P ratio of 1.90 and was prepared and maintained under substantially anhydrous conditions. The weight ratio of powder to water in the cement was between 3.5 and 4.0, with a small amount of additional liquid being supplied by bodily fluids at the wound site. The resulting cement paste was molded intraoperatively to fit the sinus defect, resulting in a successful skull repair. The patient was discharged from the hospital within three days, and on follow-up retained the sinus patch, with evidence of steadily regenerating bone replacing the implant. Other similar results were obtained in repairing bony defects of additional patients.

As the inventive materials possess remineralization capabilities the discussion above with respect to the use of the inventive compositions as cements is fully applicable to their use as remineralizers. The two main differences between the inventive remineralizers and the inventive cements are particle size and solid-to-liquid ratio. For use as a cement, the calcium phosphates are ground to specific particle sizes (e.g., relatively large TTCP and small DCPA) to achieve rapid setting and high strength, whereas for a remineralizer, the particles are ground to sizes to produce optimum release of calcium and phosphate ions into saliva and plaque to affect remineralization. Additionally, for preparation of the cements, the calcium phosphate particles are combined with much less liquid so that a paste is formed, rather than a slurry. An example of a chewing gum which utilizes the inventive composition to provide an oral slurry with remineralization potential follows.

EXAMPLE 10

A chewing gum with remineralization potential is prepared by blending the calcium phosphate cement powder (Ca/P of TTC=1.90; moles TTCP/moles DCPA=1.0) into a commercially available gum base at a 5% by weight level by hand mixing. Test subjects who chewed the calcium phosphate cement gum were sampled every two minutes up to a total of 16 minutes for the pH and calcium and phosphate levels in their saliva. The calcium and phosphate levels and the degree of supersaturation with respect to tooth mineral were found to be elevated to significantly higher extent and for a longer period than those produced by a prior art chewing gum that contained 7.5 wt % dicalcium phosphate dihydrate. Pickel et al., "The Effects of a Chewing Gum Containing Dicalcium Phosphate on Salivary Calcium and Phosphate." *Alabama Med. Soc.* 2:286–287 (1965). Similarly, the inventive compositions may be delivered e.g., via a dentifrice, rather than a chewing gum While the primary benefits of the present invention are believed to relate to dental, medical and veterinary applications, it is also contemplated that the techniques may be employed in conjunction with an industrial hydroxyapatite cement, for example, to repair damage, e.g., from corrosion, to marble and other stone articles It should be understood that the foregoing disclosure emphasizes certain specific embodiments of the invention and that all modifications or alternatives equivalent thereto are within the spirit or scope of the invention as set forth in the appended claims.

We claim:

1. Comminuted tetracalcium phosphate having a calcium to phosphate ratio less than 2 that is prepared and maintained by a process under anhydrous conditions excluding the presence of trace amounts of water including the steps of:
    (a) formulating a composition consisting essentially of tetracalcium phosphate as particles having a calcium to phosphate ratio less than 2 under anhydrous conditions excluding the presence of trace amounts of water;
    (b) subsequently reducing the particle size of said particles so that at least 10% of said particles have a particle size of $15\mu$ of less, said reducing step conducted under substantially anhydrous conditions; and
    (c) subsequently storing said particles under substantially anhydrous conditions.

2. The comminuted tetracalcium phosphate of claim 1 including the step of reducing particle size under substantially anhydrous conditions to an average particle size of $15\mu$ of less.

* * * * *